(12) United States Patent
Missling

(10) Patent No.: US 12,138,240 B2
(45) Date of Patent: *Nov. 12, 2024

(54) TREATMENT OF CARDIAC DYSFUNCTION

(71) Applicant: Anavex Life Sciences Corp., New York, NY (US)

(72) Inventor: Christopher U. Missling, New York, NY (US)

(73) Assignee: Anavex Life Sciences Corp., NY (US)

( * ) Notice: Subject to any disclaimer, the term of this patent is extended or adjusted under 35 U.S.C. 154(b) by 271 days.

This patent is subject to a terminal disclaimer.

(21) Appl. No.: 17/385,660

(22) Filed: Jul. 26, 2021

(65) Prior Publication Data

US 2022/0096424 A1    Mar. 31, 2022

Related U.S. Application Data

(62) Division of application No. 16/166,732, filed on Oct. 22, 2018, now Pat. No. 11,071,723.

(60) Provisional application No. 62/574,913, filed on Oct. 20, 2017.

(51) Int. Cl.
| | | |
|---|---|---|
| *A61K 31/34* | (2006.01) | |
| *A61K 31/341* | (2006.01) | |
| *A61P 9/00* | (2006.01) | |
| *A61P 9/06* | (2006.01) | |

(52) U.S. Cl.
CPC ............ *A61K 31/34* (2013.01); *A61K 31/341* (2013.01); *A61P 9/00* (2018.01); *A61P 9/06* (2018.01)

(58) Field of Classification Search
CPC ......... A61K 31/34; A61K 31/341; A61P 9/00; A61P 9/06
See application file for complete search history.

(56) References Cited

U.S. PATENT DOCUMENTS

| 9,931,333 | B2 | 4/2018 | Arora et al. |
| 11,071,723 | B2 * | 7/2021 | Missling ............... A61P 9/00 |
| 2011/0281853 | A1 | 11/2011 | Arora et al. |

FOREIGN PATENT DOCUMENTS

| AU | 2018351088 A1 | 5/2020 |
| GR | 1005865 B | 4/2008 |
| GR | 1008233 B | 6/2014 |
| WO | 2008087458 A2 | 7/2008 |
| WO | 2011143457 A2 | 11/2011 |
| WO | 2014155138 A1 | 10/2014 |

OTHER PUBLICATIONS

International Preliminary Report on Patentability for International Application No. PCT/US2018/056876, mailed Apr. 30, 2020, 7 pages.
International Search Report and Written Opinion for International Application No. PCT/US2018/056876, mailed Jan. 3, 2019, 9 pages.
"Chapter 21—Bootstrapping Regression Models," Exhibit B, pp. 587-606.
Lunt M., "Introduction to Statistical Modelling: Linear Regression," Exhibit C, Rheumatology, Jul. 2015, vol. 54, No. 7, pp. 1137-1140.
Malik M., "Themed Section: QT Safety Commentary: Facts, Fancies and Follies of drug-induced QT/QTc Interval Shortening," British Journal of Pharmacology, 2010, vol. 159, pp. 70-76.
Stolyaruk V.N., et al., "Effects of Afobasol in the Reperfusion Arrhythmia model," Rossiiskaya Akademiya Meditsinskikh Nauk. Vestnik, Izdatel'stvo Meditsina, Jan. 1, 2010, vol. 4, 1 Page, XP009509914, ISSN: 0869-6047 abstract.
Stolyaruk V.N., et al., "Investigation of Afobasol Anti Fibrillation Activity in Animals with the Intact and Denervated Myocardium," Rossiiskaya Akademi Va Meditsi Nski Kh Nauk.Vestnik. Izdatel'stvo Meditsina, Jan. 1, 2010, vol. 4, 1 Page, XP009509912, ISSN: 0869-6047abstract.
Vinet A., et al., "Estimation of the QT-RR Relation: Trade-Off between Goodness-Of-Fit and Extrapolation Accuracy," Exhibit A, Physiological Measurement, Mar. 2017, vol. 38, No. 3, pp. 397-419.
Examination Report No. 1 for Australian Application No. 2018351088, mailed on Sep. 14, 2023, 4 pages.

* cited by examiner

*Primary Examiner* — Sun Jae Yoo
(74) *Attorney, Agent, or Firm* — POLSINELLI PC

(57) ABSTRACT

A method for treatment of cardiac dysfunction comprising administering to a subject in need thereof a therapeutically effective amount of at least one of ANAVEX 2-73 or ANAVEX 19-144 or a pharmaceutically acceptable salt thereof or a combination thereof.

16 Claims, 19 Drawing Sheets

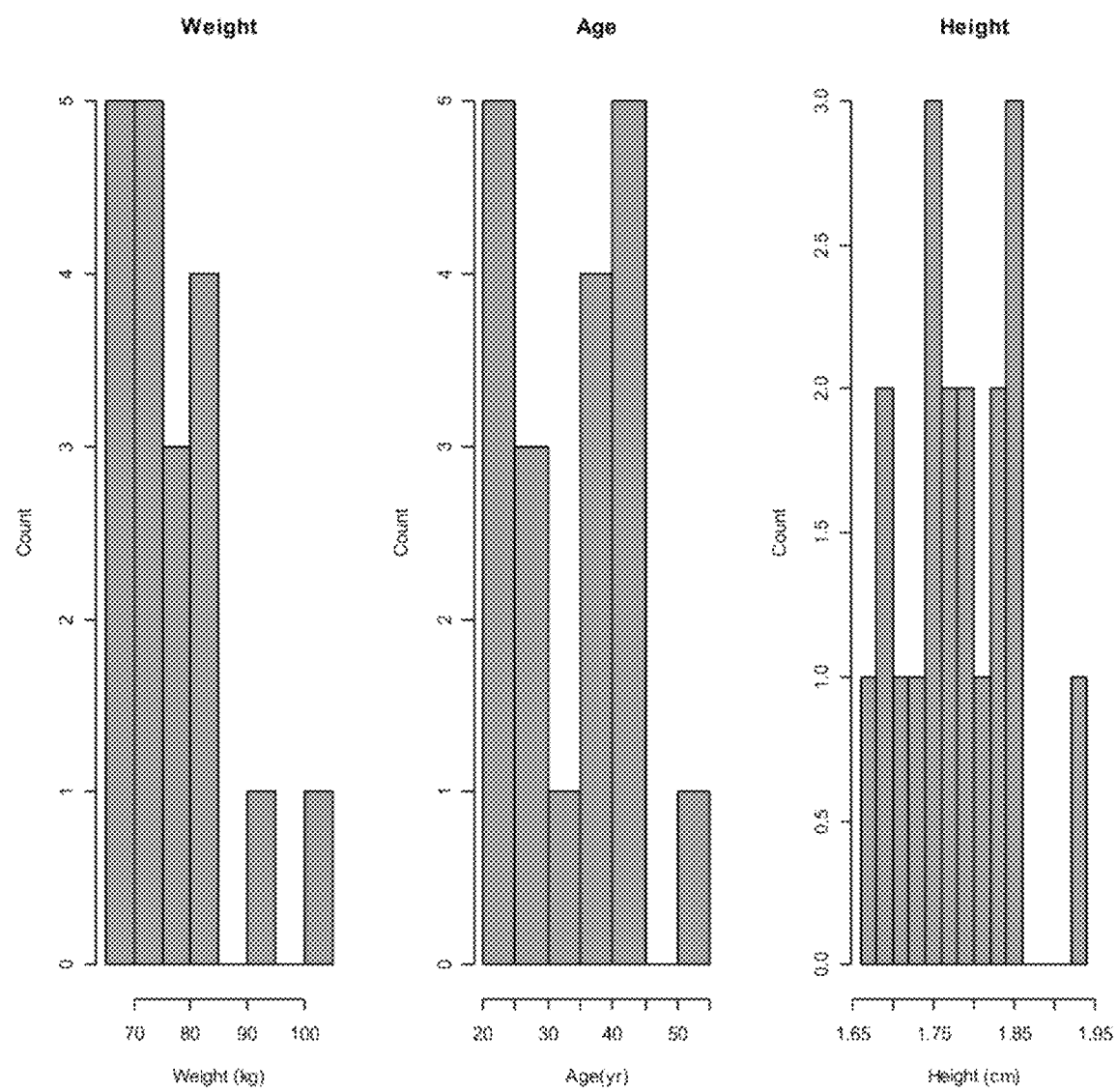

Base Model

Final Model

TREATMENT OF CARDIAC DYSFUNCTION

CROSS-REFERENCE TO RELATED APPLICATIONS

This application is a Divisional of U.S. patent application Ser. No. 16/166,732, filed Oct. 22, 2018, which claims the benefit of U.S. Provisional Patent Application No. 62/574,913 filed Oct. 20, 2017, the entire disclosures of which are hereby incorporated by reference.

FIELD OF THE INVENTION

Disclosed herein are methods of treating cardiac arrhythmias, and for the prevention subsequent cardiac arrhythmias, e.g., ventricular tachycardia or ventricular fibrillation. Particular note is made of agents, which shorten the QT interval. Agents include ANAVEX® 2-73 and ANAVEX® 19-144.

BACKGROUND

Cardiac arrest, also known as cardiopulmonary arrest, is an abrupt cessation of pump function in the heart, and cessation of normal circulation of the blood due to failure of the heart to contract effectively. Cardiac arrest can be caused by a variety of factors including, e.g., coronary heart disease, hypertension, myocardial infarction and ischemia, atrial and ventricular arrhythmias (including fibrillation and flutter), and heart failure.

Cardiac arrest is often associated with ventricular arrhythmias ("VA"), e.g., ventricular tachycardia ("VT") and/or ventricular fibrillation ("VF").

Arrhythmias are reported to occur in the upper chambers of the heart, (atria), or in the lower chambers of the heart, (ventricles). Arrhythmias may occur at any age. Some are barely perceptible, whereas others can be more dramatic and can even lead to cardiac arrest and sudden cardiac death.

In adults and children over 15, resting heart rate faster than 100 beats/minute is labelled tachycardia. Tachycardia may result in palpitation; however, tachycardia is not necessarily an arrhythmia. Increased heart rate is a normal response to physical exercise or emotional stress. This is mediated by the sympathetic nervous system on the sinus node and called sinus tachycardia. Other things that increase sympathetic nervous system activity in the heart include ingested or injected substances, such as caffeine or amphetamines, and an overactive thyroid gland (hyperthyroidism).

In cardiology, the QT interval is a measure of the time between the start of the Q wave and the end of the T wave in the heart's electrical cycle. The QT interval represents electrical depolarization and repolarization of the ventricles. A lengthened QT interval is a marker for the potential of ventricular tachyarrhythmias like torsades de pointes and a risk factor for sudden death. Like the R-R interval, the QT interval is dependent on the heart rate in an obvious way (i.e., the faster the heart rate, the shorter the R-R interval and QT interval) and may be adjusted to improve the detection of patients at increased risk of ventricular arrhythmia. RR is the interval from the onset of one QRS complex to the onset of the next QRS complex, measured in seconds, often derived from the heart rate (HR) as 60/HR (here QT is measured in milliseconds).

Definitions of normal QTc vary from being equal to or less than 0.40 s (≤400 ms), 0.41 s (≤410 ms), 0.42 s (≤420 ms) or 0.44 s (≤440 ms). For risk of sudden cardiac death, "borderline QTc" in males is 431-450 ms; and, in females is 451-470 ms. An "abnormal" QTc in males is a QTc above 450 ms; and, in females is a QTc above 470 ms.

Reference is made to Fridericia's QT interval correction formula using the cube-root of RR:

$$QTcF = \frac{QT}{\sqrt[3]{RR}}.$$

The compound 1-(2,2-diphenyltetrahydrofuran-3-yl)-N-methylmethanamine hydrochloride (ANAVEX® 19-144, or A19-144) is believed to bind to muscarinic acetylcholine and sigma-1 receptors with affinities in the low micromolar range. ANAVEX®2-73 (also termed A2-73) has a systematic name 1-(2,2-diphenyltetrahydrofuran-3-yl)-N,N-dimethylmethanamine hydrochloride and displays similar activity.

SUMMARY OF THE INVENTION

This disclosure comprises a method for treatment of cardiac dysfunction comprising administering to a subject in need thereof a therapeutically effective amount of at least one of ANAVEX 2-73 or ANAVEX 19-144 or pharmaceutically acceptable salt thereof or combination thereof. Particular note is made of treatment which shortens the QT interval. In particular embodiments the shortening of the QT interval is about 10 ms or about 2% to about 3% as shown in FIGS. 8 and 9.

In one embodiment the method, the cardiac dysfunction treated is selected from the group comprising cardiac arrest-related dysfunction including cardiac arrhythmia, premature ventricular contraction (PVC) induced left ventricular dysfunction, atrial fibrillation, atrial flutter, induced left ventricular dysfunction, ventricular arrhythmia including ventricular tachycardia and fibrillation, and a combination thereof. Particular reference is made to treating ventricular arrhythmia and atrial arrhythmia.

In particular embodiments the method encompasses administering to a subject a therapeutically effective amount of ANAVEX2-73 daily, with particular reference to administering oral doses of about 20 to about 60 mg or intra venous doses of about 6 mg to about 17 mg. In some embodiments this consists of two daily oral doses of about 20 mg, and in other embodiments two daily doses of about 30 mg each. In other embodiments a single daily oral dosage of about 40 mg or 60 mg is administered. In some embodiments intravenous administration comprises daily doses of about 8 mg, about 10 mg and about 15 mg of ANAVEX2-73.

Also noted are embodiments of method encompassing administering to a subject a therapeutically effective amount of ANAVEX19-144 daily, with particular reference to orally administering from about 20 mg to about 60 mg, including two daily doses of about 20 mg or 30 mg each or intra venous doses of about 6 mg to about 17 mg. In other embodiments a single daily oral dosage of about 40 mg or about 60 mg is administered. In some embodiments intravenous administration comprises daily doses of about 8 mg, about 10 mg and about 15 mg of ANAVEX19-144.

BRIEF DESCRIPTION OF THE DRAWINGS

FIG. 1A-C presents a graph of distributions of the continuous demographic covariates:

FIG. 1A weight, FIG. 1B age, FIG. 1C height.

FIG. 13A-B is a linear exposure-QTcF model with all the variables (parent, metabolite, and time) wherein FIG. 13A is the base model and FIG. 13B is the final model.

FIGS. 15 A-F are plots of the relationship among Model Covariates and Conditioning Weighted Residuals wherein

FIGS. 17A-F show a relationship between Model Covariates for the Exposure-Heart Rate Model and Conditioning Weighted Residuals wherein FIG. 17A is a Based Model Plot for A2-73, FIG. 17B is a Final Model for A2-73, FIG. 17C is a Based Model Plot for A19-144, FIG. 17D is a Final Model for A19-144, FIG. 17E is a Based Model Plot based on Time, and FIG. 17F is a Final Model based on Time.

DETAILED DESCRIPTION

Figure 2A:
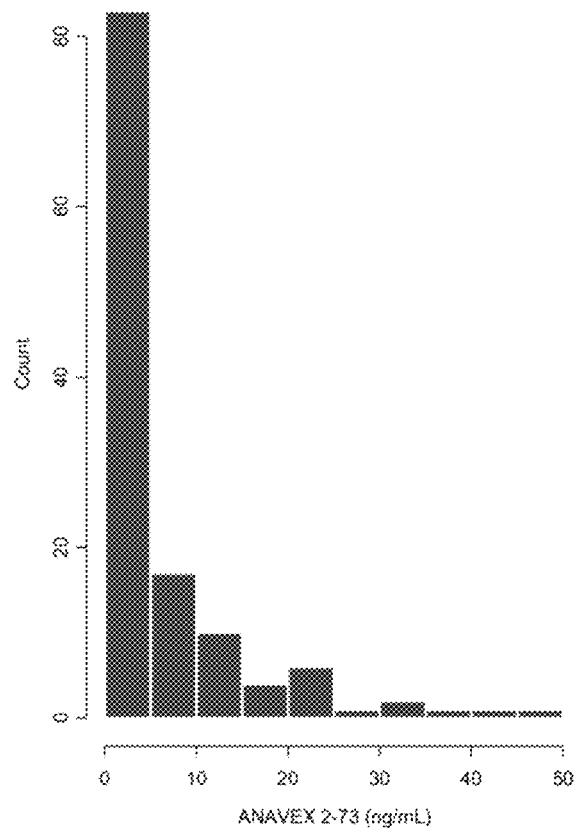
FIG. 2A-B presents a graph of distributions of A2-73 (FIG. 2A) and A19-144 (FIG. 2B).

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. Ranges from any lower limit to any upper limit are contemplated. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Although any methods and materials similar or equivalent to those described herein can also be used in the practice or testing of the present invention, the preferred methods and materials are now described. All publications mentioned herein are incorporated herein by reference in their entirety.

All numerical values within the detailed description and the claims herein are modified by "about" or "approximately" the indicated value, and take into account experimental error and variations that would be expected by a person having ordinary skill in the art.

This disclosure will be better understood with reference to the following definitions:

B. Par. Est. Bootstrap parameter estimate
BQL below the quantifiable limit
BSE bootstrap standard error
CL/F apparent clearance
Conc concentration
CWRES conditional weighted residuals
CWRESI conditional weighted residuals with interaction
dQTcF/ΔΔQTcF change in QTcF from baseline
DV dependent variable (observed concentrations)
E QTc response
EC50 concentration producing 50% of maximal change in QTc
ECG electrocardiogram
E max Maximal change in QTc
FDA Food and Drug Administration
FO first order
FOCE first order conditional estimation
FOCEI first order conditional estimation with interaction
hr hour(s)
HV healthy volunteer
IIV interindividual variability
IPRED individually predicted concentrations
kg kilogram(s)
LLD log-likelihood difference
LOQ limit of quantification
mg milligram(s)
mL milliliter(s)
ng nanogram(s)
NONMEM nonlinear mixed effects modeling software program
NPDE Normalized prediction distribution errors
OFV objective function value
PK pharmacokinetics
PPK population pharmacokinetics
PRED population predicted concentrations
PSN Perl Speaks NONMEM
QTcF heart rate-corrected QT interval according to Fridericia's formula
RSE relative standard error
SE standard error
VPC visual predictive check
yr year(s).

Without being bound by any particular theory, ANAVEX19-144 is reported as a metabolite of ANAVEX2-73. In the present disclosure ANAVEX2-73 is a compound, which is subjected to enzymatic oxidation, reduction or hydrolysis under physiological conditions in the living body, and is converted to ANAVEX19-144 of the present disclosure.

Seventeen subjects contributed ECG data to the analysis dataset. The study was randomized single dose escalating phase I first-in-human study designed to investigate the safety and tolerability, and pharmacokinetics of ascending oral doses of ANAVEX 2-73 in male healthy subjects. It was double-blind and placebo-controlled within each dosage step—a two cohort study with alternating single dose escalation performed in male healthy subjects. Subjects were administered 10, 30, 40, 50, or 60 mg of ANAVEX 2-73 orally with a 4-week washout between doses. Sampling for drug and ECG was from predose to 48 hr. Note that Placebo-adjusted (delta-delta) change in QTcF is represented as ΔΔQTcF.

Subjects provided time-matched exposure-ECG data for analysis. For the exposure-QTc analysis, data obtained after the administration of doses greater than 1 mg were used. Data from the 1 mg dose were excluded because the concentration of ANAVEX 2-73 was not quantifiable at most of the sampling times beyond two to four hours after dosing and ANAVEX 19-144 concentrations were all below the limit of detection. However, ECG data from the administration of the 1 mg dose were included in the categorical and outlier analysis.

Analysis

Data analysis proceeded from data structure analysis in S-PLUS to linear/nonlinear mixed effects modeling in NONMEM to develop the exposure-QTc relationship for ANAVEX 2-73 and its active metabolite ANAVEX 19-144. The correction method used for QT interval was the Fridericia's correction. The bootstrap was used to determine the reliability/stability of the exposure-QTc models developed. This was necessary to determine if the modeling results obtained with data from the 17 subjects would be applicable to the population at large, given the sample size. Exposure-heart rate and exposure-change from baseline QTc, and exposure-placebo corrected QTc relationship models were developed for the elucidation of any exposure-QTc relationship.

Moreover, the mixed effects model averaging approach was also used to characterize the exposure-QTc relationship, and the cut-off criteria were used to delineate a 'top model set' are the top two corrected Aikaike Information criterion (AICc) models and 95% confidence (summed weight). These were used to determine the top model set used to compute the model-averaged parameters. Additionally, there are two methods by which the estimate and error for each parameter are weighted. These are: the natural average method and the zero method. The natural average method is used to produce conditional coverage parameter estimates, while the zero method is used to produce full coverage parameters estimates. The zero method decreases the effect sizes (and errors) of predictors that only appear in models with small model weights (particularly when the predictors have weak effects), diluting the parameter estimates of these predictors (shrinkage towards zero).

In addition, categorical summaries of the ECG data were generated using the ICH E14 guidance-defined categories of QTc interval duration as well as change from baseline.

These data are summarized as follows:

A categorical analysis by time point indicated that across sampling times Fridericia corrected QTc (i.e., QTcF) values were consistently <450 ms, including the baseline for doses from 10 to 60 mg. One subject who received a 1 mg dose had QTcF of 450 ms at one time point (36 hr). This occurred 34 hr after ANAVEX 2-73 concentration was below the limit of detection, and ANAVEX 19-144 was not detectable in the subject.

No subject had dQTcF >30 ms at any time point.

Two-sided 90% CI in dQTcF indicated that the upper limit of the 90% CI fell below 20 ms at each time point, except for one subject at the 40 mg dose when the concentration of ANAVEX 2-73 was 2.23 ng/mL and that of ANAVEX 19-144 was 3.33 ng/mL at the 24 hr time point, and another subject at the 1 mg dose level at the 36 hr time point. For the latter subject, ANAVEX 2-73 concentration was below the limit of quantification after 2 hr. There was no quantifiable concentration of ANAVEX 19-144. There was no apparent delayed QTc response with counter-clockwise hysteresis.

The characterization of exposure-dQTcF did not show any effect of ANAVEX 2-73 and ANAVEX 19-144 on dQTcF.

ANAVEX 19-144 is anti-arrhythmic.

There was no relationship between ANAVEX 2-73 and ANAVEX 19-144 on ΔΔQTcF.

Overall, ANAVEX 2-73 administration does not prolong QT interval. This is irrespective of whether the forward/backward stepping frequentist approach or the information theoretic model averaging approach was used to analyze the data.

Overall, QTc interval tended to decrease with time and leveled off over the observation period after ANAVEX 2-73 administration.

A protocol presented herein was a single ascending dose (SAD) phase I first-in-human study designed to investigate the safety and tolerability, and pharmacokinetics of ascending oral doses of ANAVEX 2-73 in male healthy subjects. The study was a randomized, double-blind, and placebo-controlled within each dosage step. It was a two cohort study with alternating single dose escalation performed in male healthy subjects. The subjects were divided into two cohorts of 8 subjects each—Cohort A (n=8), and Cohort B (n=8). However, 17 evaluable subjects were studied in a 8:9 ratio in cohorts A and B, respectively. The study comprised repeated treatment periods with at least 4 weeks of intermediary washout periods.

Blood samples for ANAVEX 2-73 and metabolite ANAVEX 19-144 plasma concentration determination were drawn on Day 1 at time zero, T0, (before drug administration), T+0.25 h (15 min), T+0.5 h (30 min), T+1 h, T+1.5 h, T+2 h, T+3 h, T+3.5 h, T+4 h, T+6 h, T+8 h and T+12 h, on Day 2 at T+24 h and T+36 h, and on Day 3 at T+48 h.

Per study protocol, triplicate 12-lead ECGs safety recordings were obtained at the following times: Day 1 at T0/predose (3 baseline ECGs), T+0.25 h (15 min), T+0.5 h (30 min), T+1 h, T+2 h, T+4 h, T+8 h and T+12 h, on Day 2 at T+24 h, T+36 h, and on Day 3 at T+48 h. ECGs were recorded at each PK sampling time (i.e., 0.25, 0.5, 1, 2, 3, 4, 6, 8, 24, 36, and 48 hours after initiation of treatment). Thus, ECG recordings were time-matched with PK sampling.

The PK variables employed in the analysis were the patient-, regimen- and time-specific observed plasma concentration of ANAVEX 2-73 and ANAVEX 19-144.

ECG metrics evaluated included the heart rate (HR), the duration of QT interval, and the heart rate-corrected QT interval according to Fridericia's formula (QTcF). Change of QTcF from baseline (dQTcF), and placebo corrected QTcF (ΔΔQTcF) were generated from the data and used for the analysis.

The ECG evaluable population included all subjects who received at least one dose of study drug (1, 10, 30, 40, or 60 mg), predose baseline ECG, and at post-dose ECG assessments.

The concentration-QTc evaluable population included all patients in the ECG evaluable population for whom at least one matching PK-ECG pair was available post-dose. However, data for the 1 mg dose were excluded in the exposure-QTc analysis because concentrations of ANAVEX 2-73 were available for up to 2 to 4 hr and subjects had between 2 to 4 unquantifiable concentrations of the drug. ANAVEX 19-144 concentrations were not quantifiable after the administration of the 1 mg dose.

As shown in Table 1, 17 subjects had evaluable time-matched concentration-QTc measurements across the study sampling duration.

TABLE 1

Analysis Population by Dose Levels (N = 17 Patients)

| Population | ANAVEX 2-73 Dose | | | | |
|---|---|---|---|---|---|
| | 10 mg | 30 mg | 40 mg | 60 mg | Total |
| ECG | 88 | 82 | 21 | 39 | 230 |
| Concentration-QTc pairs | 88 | 82 | 21 | 39 | 230 |
| *Subjects by dose | 8 | 8 | 2 | 4 | 17 |

*Only 14 unique subjects exposed to drug administration had measurable parent drug and metabolite concentrations.

The three replicate ECGs were recorded at each nominal time point were supplied as mean observations and used as such for statistical evaluations and exposure-QTc analysis.

Baseline ECG was defined as pre-dose baseline on each dosing occasion. Given the four weeks washout between dosing, the pre-dose baseline ECG was used as the baseline ECG for the particular dose/dosing occasion. A change from baseline variable for QTc interval ($\Delta$QTcF) was calculated using pre-dose baseline.

$\Delta\Delta$QTcF data was a single dose ascending study. As such not all subjects were administered placebo in each of the study periods. Only nine subjects were administered placebo in the course of the study. Consequently, it was not possible to make subject specific placebo correction. Thus, the computation of $\Delta\Delta$QTcF was performed in three steps as follows:

Step 1: Calculation of the grand average of placebo QTcF data using data from those subjects who were administered placebo.

Step 2: Calculation of dQTcF drug at a given time as:

$dQTcF_{drug,time=t} = QTcF_{drug,time=t} - QTcF_{drug,time=0}$, and calculation of dQTcF$_{Placebo}$ at a given time as:

$dQTcF_{placebo,time=t} = QTcF_{placebo,time=t} - QTcF_{placebo,time=t}$.

Step 3: Calculation of $\Delta\Delta$QTcF as:

$\Delta\Delta QTcF_{time=t} = dQTcF_{drug,time=t} - dQTcF_{placebo,t}$.

Concentration-QTc modeling was performed with the software NONMEM v7.3 (Icon Development Solutions, Ellicott City, MD) and graphical analysis, diagnostics plots, and supporting analyses using S Plus v8.2 (TIBCO Software, Boston, MA) and the R package.

The dataset comprised observed ANAVEX 2-73 and ANAVEX 19-144 plasma concentrations that were direct matches in time with QT interval measurements. The analysis variable of interest was the QT interval duration corrected for RR interval duration according to Fridericia's formula (i.e., QTcF), HR, and change from baseline QT interval duration corrected for RR interval duration according to Fridericia's formula ($\Delta$QTcF or dQTcF). Baseline is defined as the mean of any and all values immediately obtained prior to ANAVEX 2-73 administration.

Selection of the most appropriate model was based on graphical diagnostics for non-nested models as well as the likelihood ratio test for nested models.

The approach used in characterizing exposure-QTc relationship was as follows:

1) Concentration and QTc versus time plots were examined for any apparent trends or associations.
2) Subject- and dose-specific QTc vs concentration plots were also examined for association as well as for the presence of any hysteresis indicative of temporal dissociations, i.e., indirect effects.
3) All of the QTc measurements were plotted against the paired concentration measurements. Smoothing splines or locally-weighted regression curves were superimposed to visually identify if there was any trend and the approximate shape of the trend.
4) Given the results of 1-3 above, models of the appropriate structure were fitted to the observed data. Where possible, stepwise implementation of hierarchical models was performed and models were compared using the likelihood ratio test to assess statistical significance. The prespecified α was 0.05. The simplest model that assumed a concentration effect, i.e. a linear model, was fitted first. This model was compared with a concentration-naïve model, i.e., an intercept-only model. Subsequently, one or more nonlinear models, such as the simple E max model or E max model with two sites of drug action was fitted to the data. Additionally, models incorporating cooperativity of drug action such as competitive antagonism between ANAVEX 2-73 and ANAVEX 19-144 concentrations and QTc effect were evaluated, as warranted, using nonlinear mixed effects modeling. Any presence of a hysteresis in the concentration-QTc profiles was to inform the use of a model characterizing the temporal dissociation to fit the data.

Statistical evaluations were performed using S Plus v8.2 (TIBCO Software, Boston, MA).

Continuous ECG data (QTcF, HR) were summarized using descriptive statistics (number of patients, mean, standard deviation, median, 25th and 75th percentiles, minimum, and maximum). The summaries of ECG parameters and the corresponding changes from baseline are presented at each time point. The subject- and regimen-specific listings are the average interval value at each time point.

QTcF measurements at each time point were averaged across subjects within a regimen using the arithmetic mean. The change from baseline was the mean change from baseline in QTcF at each time point. Change from baseline across all study time points were similarly calculated as described above.

A two sided, 90% CI for the mean in the $\Delta$QTcF was calculated at each time point. The 90% CI for $\Delta$QTcF was considered the primary analysis variable. The upper limit of the 90% CI [per the ICH Guidance (ICH E14 2005)] at each time point was compared to a 20 ms threshold. If the upper limit of the 90% CI fell below 20 ms at all time points, the conclusion would be that ANAVEX 2-73 is unlikely to prolong the mean QTc interval to a clinically significant degree.

ECG data were summarized categorically using the number and proportion of subjects with a maximum change from baseline in QTcF using the following categories:

>30 msec increase
>60 msec increase.

For the determination of the proportion, the denominator was the number of ECG-evaluable subjects. All subjects in the dataset were ECG evaluable.

The maximum post-treatment observed value within subject and regimen for QTcF were categorized into three groups:
>450 msec
>480 msec
>500 msec.

For the computation of the model parameter estimates, a top model set is defined and the method used to compute the model-averaged parameters is carefully chosen. There are two methods by which the estimate and error for each parameter are weighted (see Burnham K P, Anderson D R. Model Selection and Multimodel Inference: "A Practical Information-Theoretic Approach, 2nd ed". 2002. Springer, Berlin and Lukacs P M, Burnham K P, Anderson D R. "Model selection bias and Freedman's paradox," *Ann Inst Stat Math* 2010; 62: 117-125 for details). With the natural average method (Burnham 2002), the parameter estimate for each predictor is averaged only over models in which that predictor appears and is weighted by the summed weights of these models. On the other hand, with the zero method (Burnham 2002), a parameter estimate (and error) of zero is substituted into those models where the given parameter is absent, and the parameter estimate is obtained by averaging over all models in the top model set. Thus, the zero method decreases the effect sizes (and errors) of predictors that only appear in models with small model weights (particularly when the predictors have weak effects), diluting the parameter estimates of these predictors (i.e., shrinkage towards zero) (Lukacs 2010).

The IT model averaging approach was used to perform the analysis in addition to the traditional frequentist forward and backward stepping model selection approach. The purpose was to ensure that the results from the traditional hypothesis testing were not some isolated occurrences. By doing so, strong inferences are made from the results when the findings from model averaging confirm the results from the forward and backward stepping model selection approach. The results of the model averaged parameter estimates computed by the zero method (the so-called full average coefficients or estimates, (Lukacs 2010)) are reported, except where there is need to highlight a variable for biological reasons. In such a situation, the parameter estimates obtained by the natural average method (the so-called conditional average coefficients or estimates) are reported. The cut-off criterion used to delineate a 'top model set' were the top 2AICc of models and the 95% confidence (summed weight). The IT approach to model averaging using AICc and the 95% confidence (summed weight) criteria as implemented in the R packages AICcmodavg and MuMin were used to perform the analyses.

Distributions of the continuous demographic covariates are in FIG. 1. In addition, a statistical summary of demographic data of subjects who contributed data to the analysis dataset is contained in Table 2.

TABLE 2

A Statistical Summary of Demographic Data

| Covariate | Summary |
| --- | --- |
| Age (yr) | n = 17 |
| Mean (SD) | 35.1 (9.18) |
| Median (Min, Max) | 39.0 (20.0, 51.0) |

TABLE 2-continued

A Statistical Summary of Demographic Data

| Covariate | Summary |
| --- | --- |
| Weight (kg) | n = 17 |
| Mean (SD) | 77.5 (9.36) |
| Median (Min, Max) | 76.5 (65.0, 103) |
| Height (cm) | n = 17 |
| Mean (SD) | 1.79 (0.0663) |
| Median (Min, Max) | 1.79 (1.66, 1.93) |
| Gender n (%) | n = 17 |
| Male | 100% |

Figure 2B:
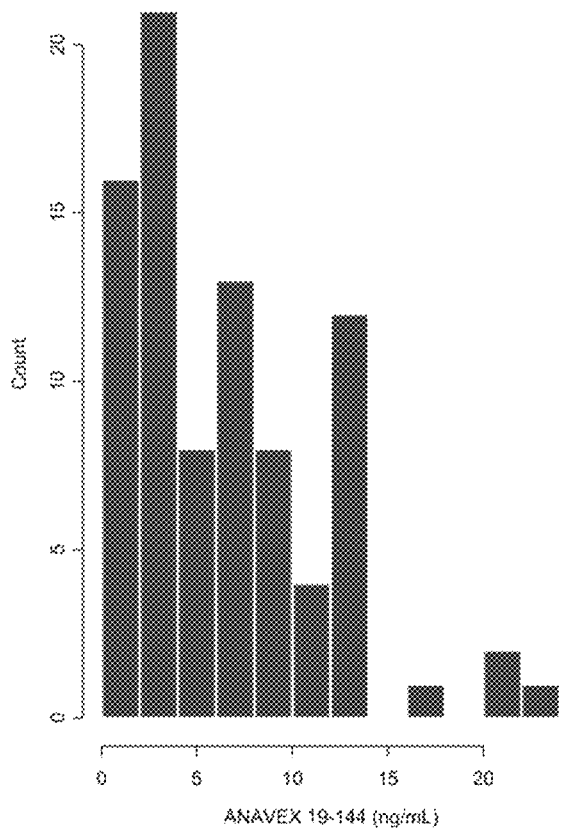

Exposure analysis is explained as follows: The distribution of concentrations of ANAVEX 2-73 and ANAVEX 19-144 are presented in FIGS. 2A and 2B respectively. The concentration of ANAVEX 2-73 ranged from 0.23 to 46.25 ng/mL. The range of concentrations for the ANAVEX 19-144 was from 0.18 to 23.96 ng/mL.

Figure 3:
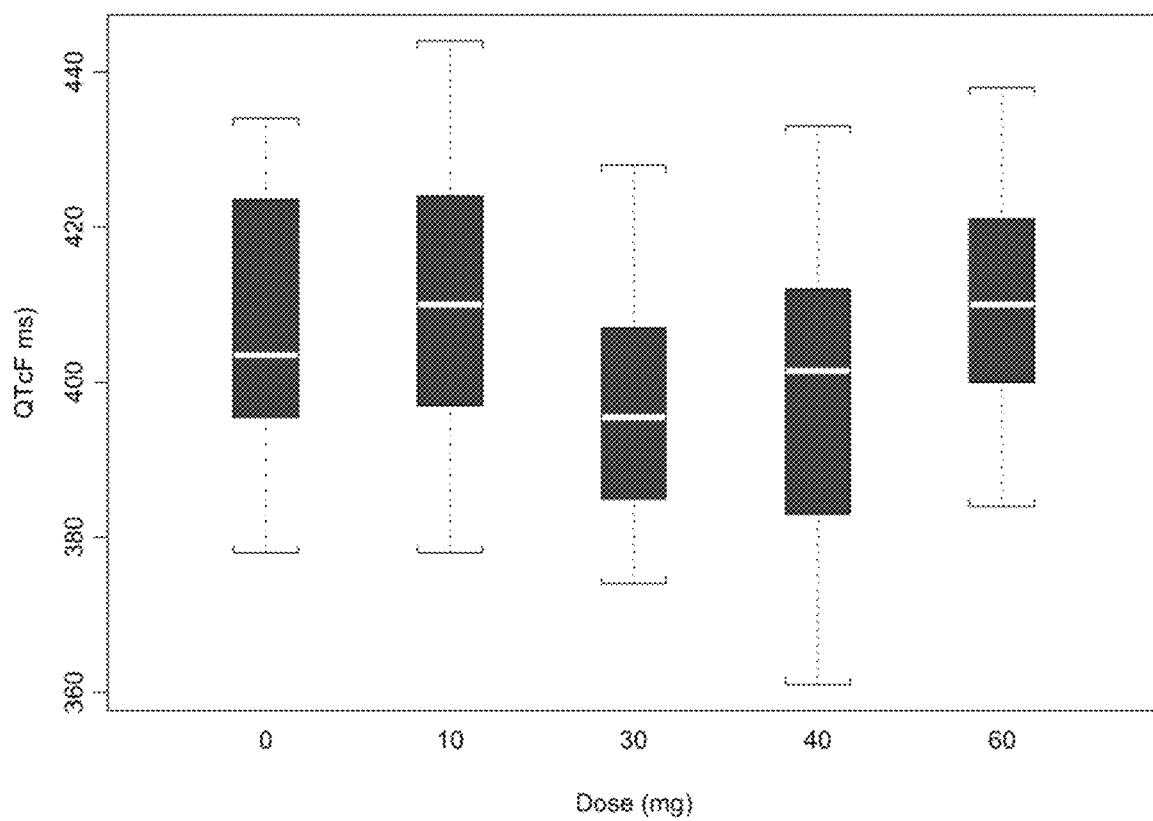
FIG. 3 is a plot of the QTcF by dose.
Figure 4:
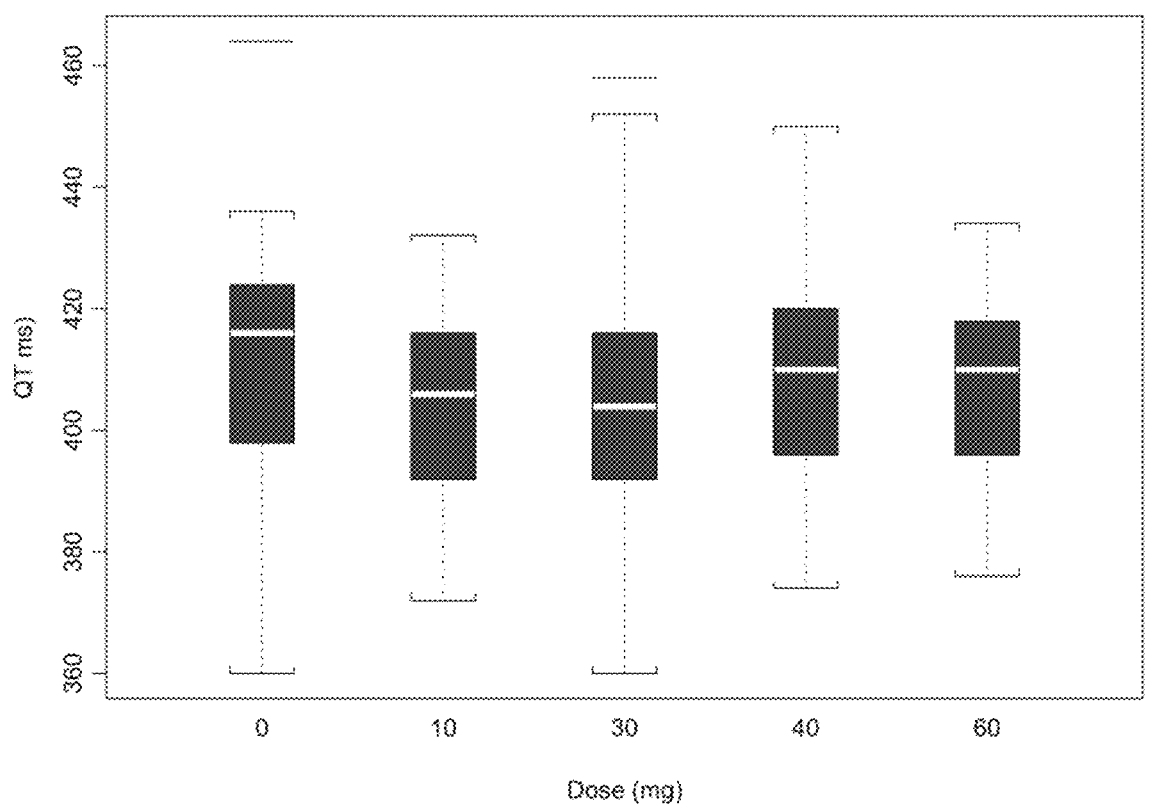
FIG. 4 is a plot of distribution of QTcF by dose.
Figure 5:
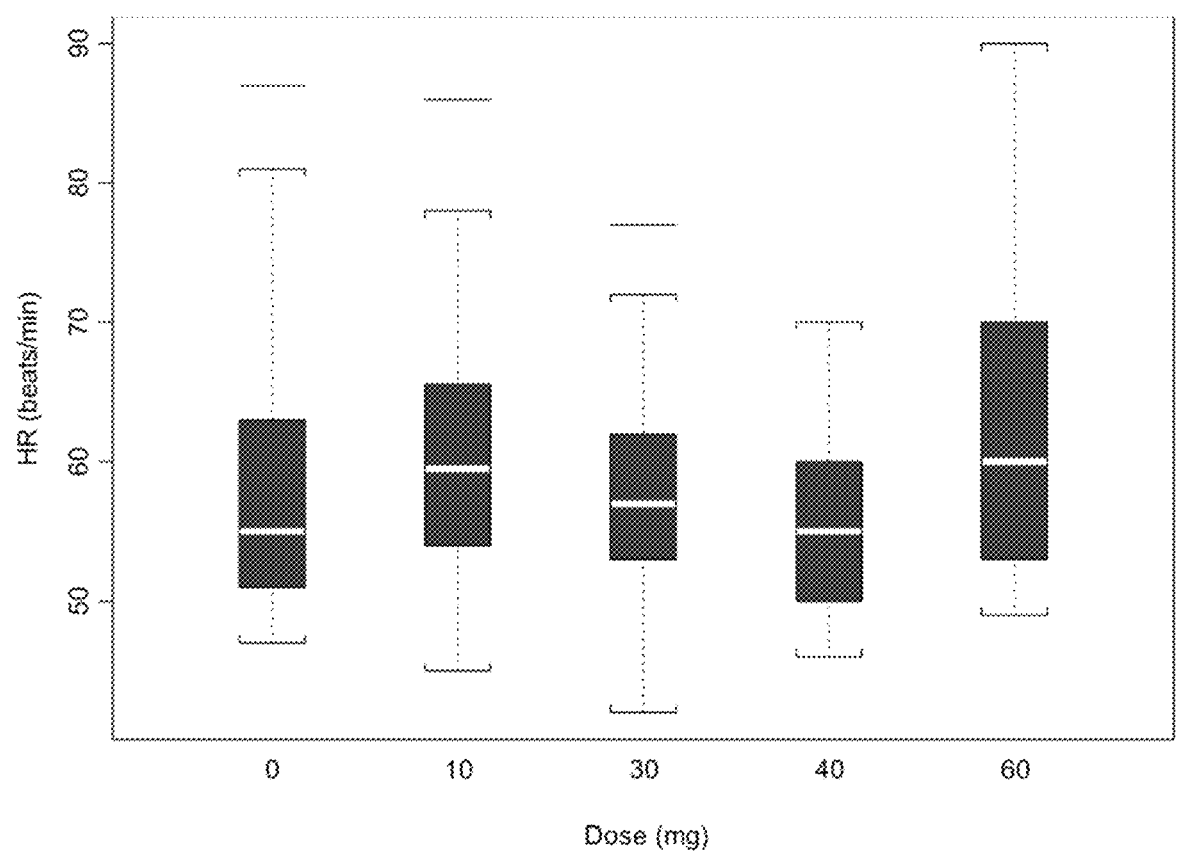
FIG. 5 is a plot of distribution of heart rate by dose.

FIG. 3 is a plot of the QTcF by doses. The QT interval appeared to decrease below the baseline at the 10 and 30 mg doses with a return to baseline at the 40 and 60 mg doses (FIG. 4). The pattern for heart rate (HR), on average, appeared to be a reverse of the pattern with QT interval as shown in FIG. 5.

Figure 6A:
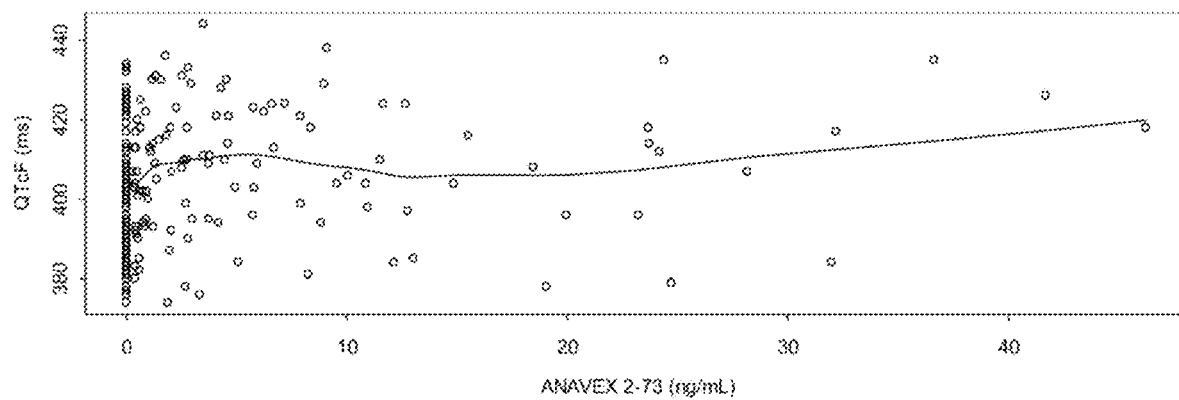
FIG. 6A-B is a plot of the relationship of ANAVEX 2-73 (FIG. 6A) and ANAVEX 19-144 (FIG. 6B) exposure with QTcF.
Figure 6B:
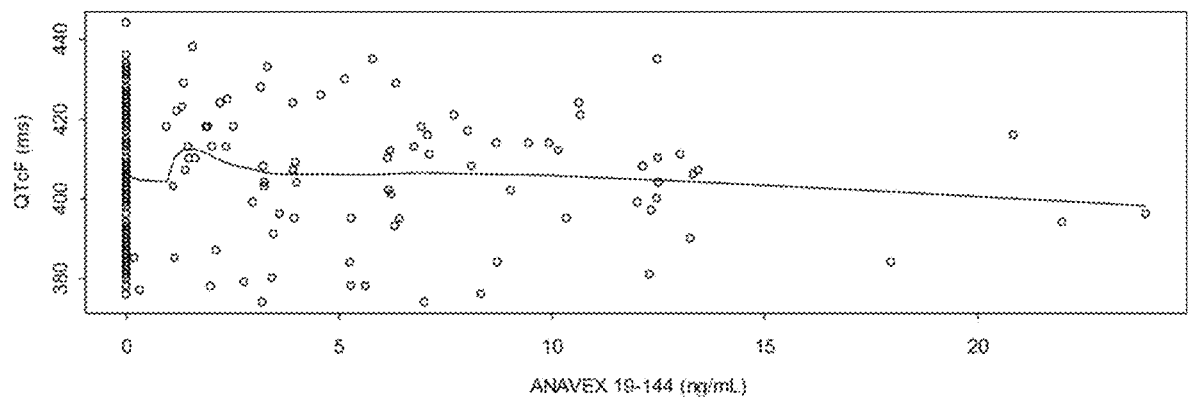

A graphical analysis of the relationship between paired ANAVEX 2-73 concentrations with QTcF measurements tended to suggest a minimal positive trend due to three points in the 35 to 46 ng/mL concentration range (FIG. 6A). A similar plot of paired ANAVEX 19-144 concentrations with QTcF measurements suggest a slight minimal upward trend from baseline followed by a slight negative trend (FIG. 6B). There is a return to baseline value at concentration of approximately 10 ng/mL for ANAVEX 2-73, and at about 5 ng/mL for the metabolite. The trend continued in the original positive or downward direction at 25 and 12 ng/mL of parent compound (FIG. 6A) or metabolite (FIG. 6B), respectively. Note that the unbroken line is a locally weighted regression (smoothing) line.

Figure 7:
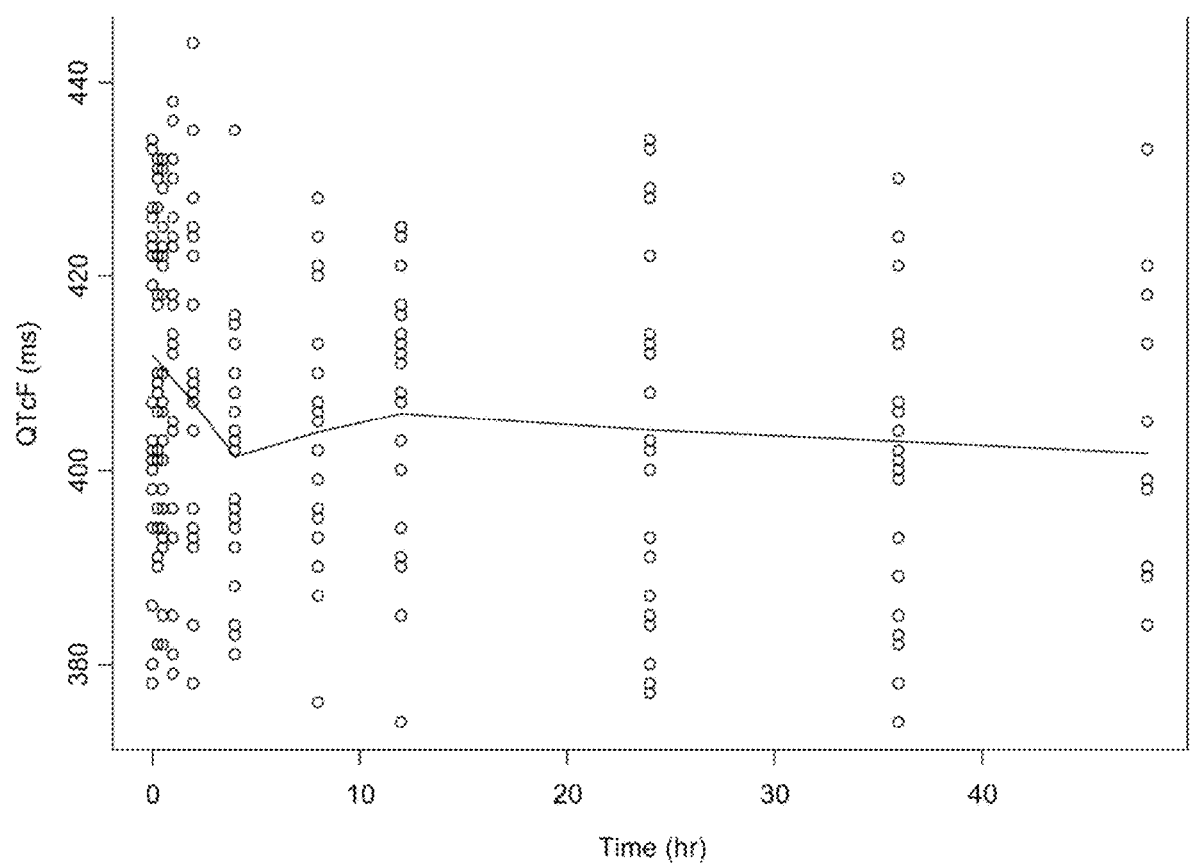
FIG. 7 is a plot of QTcF over time from A2-73 administration.
Figure 8:
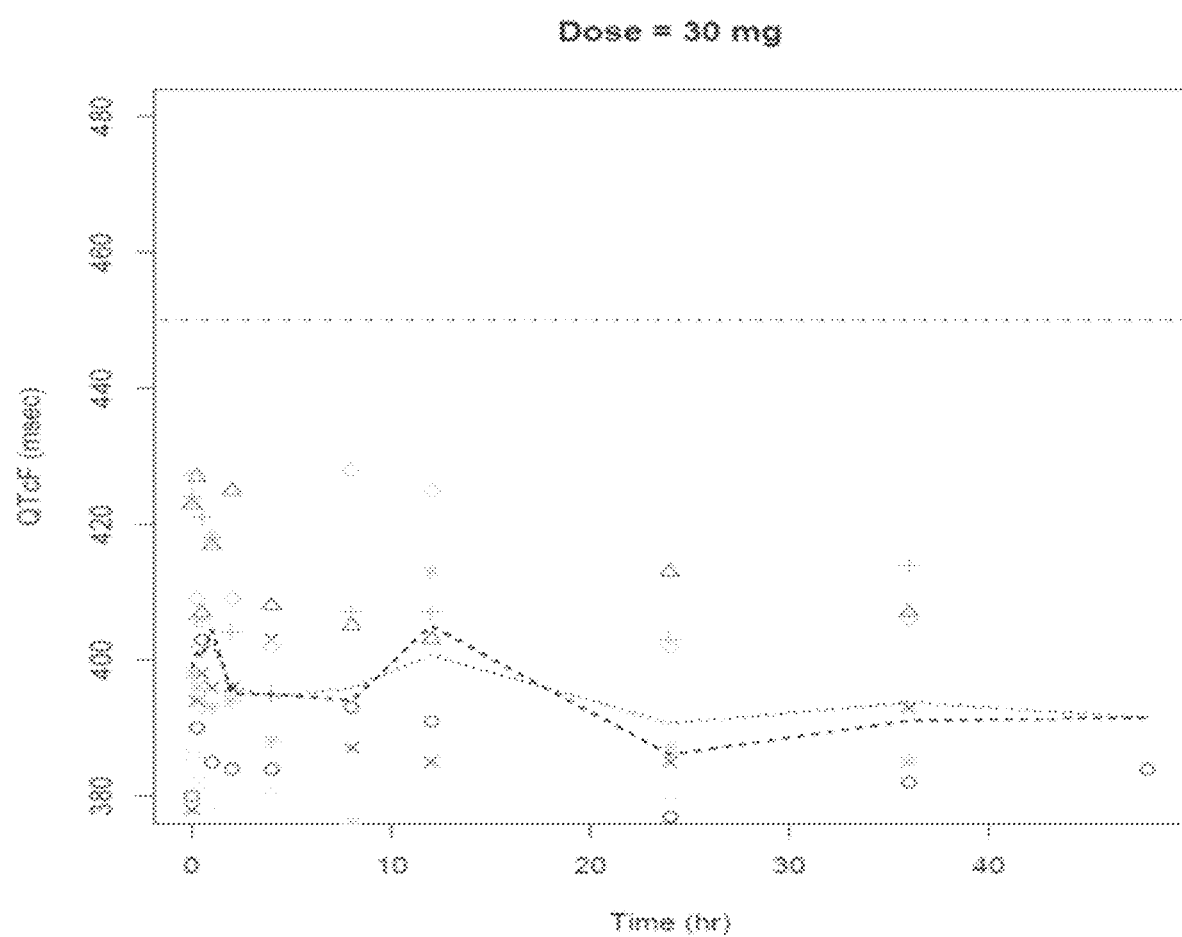
FIG. 8 is a plot of QTcF over time from A2-73 for 30 mg administration.
Figure 9:
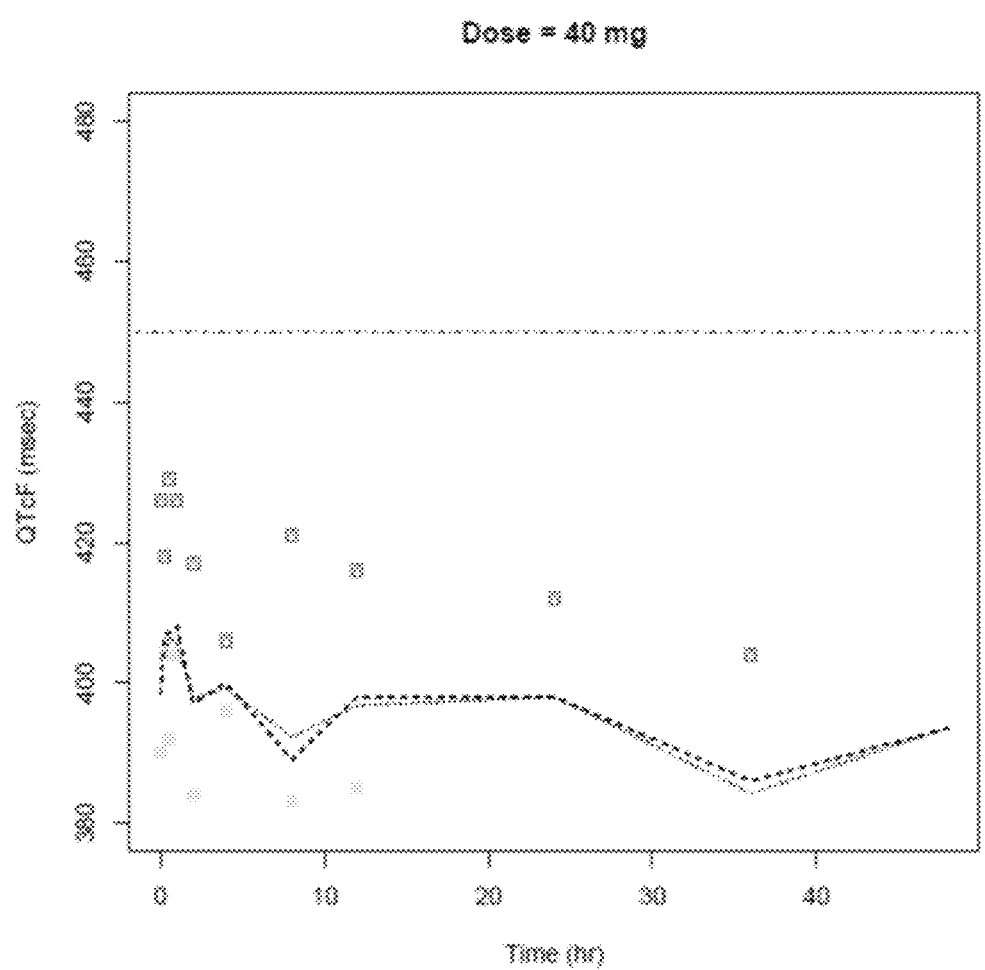
FIG. 9 is a plot of QTcF over time from A2-73 for 40 mg administration.

Overall, QTc interval tended to decrease with time and leveled off over the observation period after A2-73 administration (FIG. 7). The unbroken line in FIG. 7 is a locally weighted regression (smoothing) line indicating the general trend of QTcF over time after ANAVEX 2-73 administration. This trend can be clearly seen with the 30 and 40 mg doses (FIG. 8 and FIG. 9, respectively). Black dotted line is the mean line, and grey dotted line is the median line. The horizontal dotted line is the 450 ms cut-off line for outlier. Different colors or symbols represent QTcF values for different subjects who were administered 30 mg (FIG. 8) or 40 mg (FIG. 9) of ANAVEX 2-73.

Figure 10:
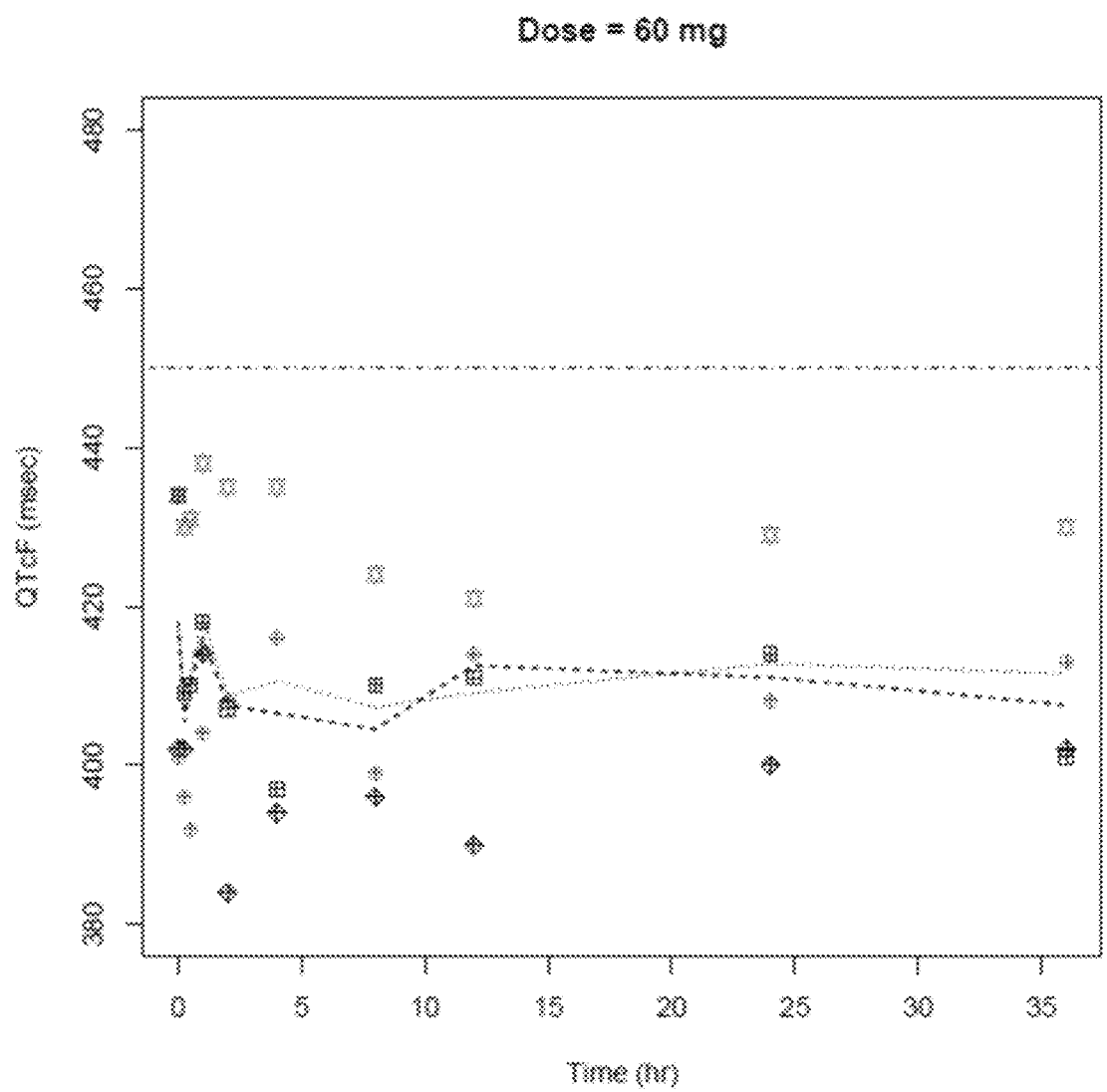
FIG. 10 is a plot of QTcF over time from A2-73 for 60 mg administration.
Figure 11:
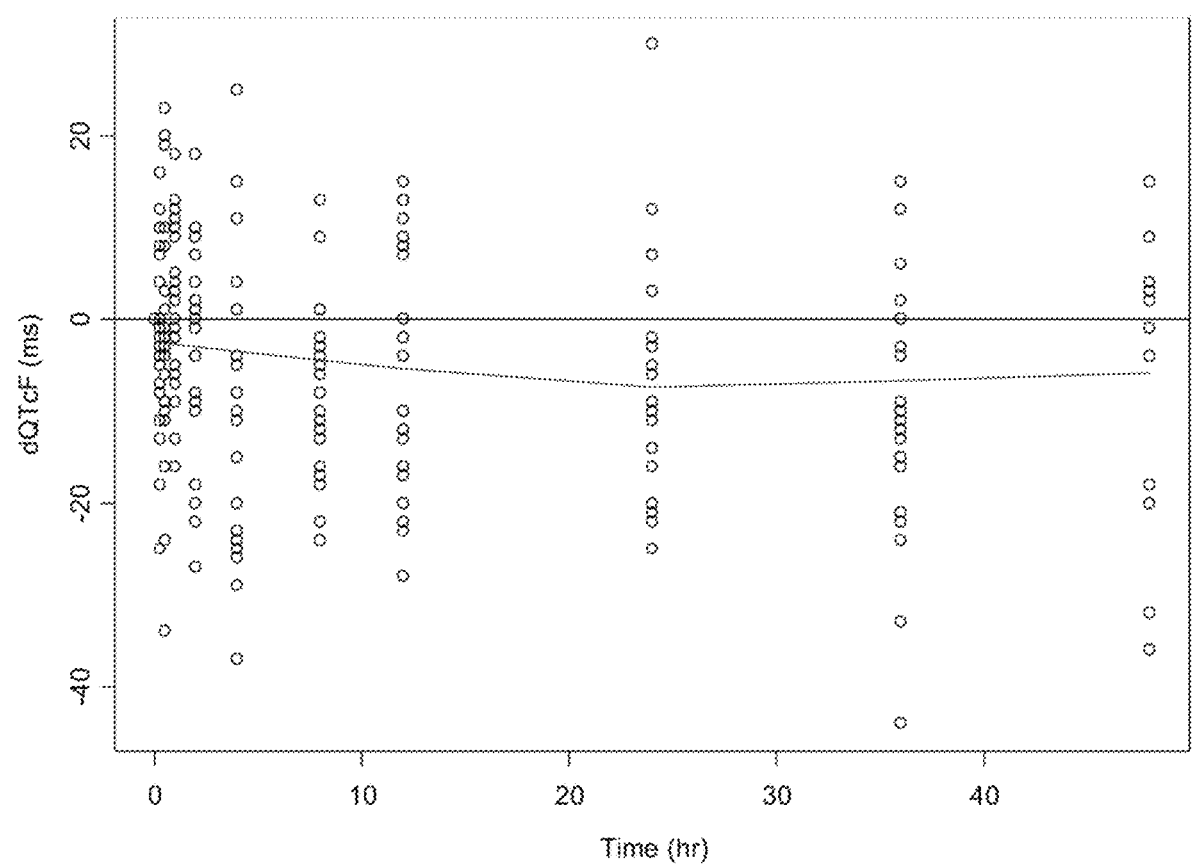
FIG. 11 is a plot of dQTcF over time from A2-73 administration.

FIG. 10 is similar plot for the 60 mg dose shows that the QTc interval remained stable over the observation period. The black dotted line is the mean line, and grey dotted line is the median line. The horizontal dotted line is the 450 ms cut-off line for outlier. Different colors or symbols represent QTcF values for different subjects who were administered 60 mg of ANAVEX 2-73. The pattern seen in the relationship of QTcF with time holds true in the relationship of dQTcF with time, as expected as shown in FIG. 11.

Figure 12A:
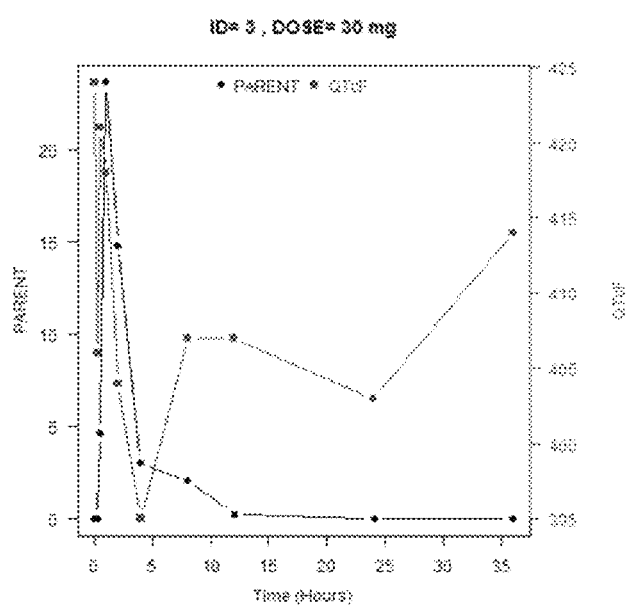
FIG. 12A-B is presents a relationship between ANAVEX 2-73 (FIG. 12A) and ANAVEX19-144 (FIG. 12B) exposure and QTc over time at the 30 mg dose level.
Figure 12B:
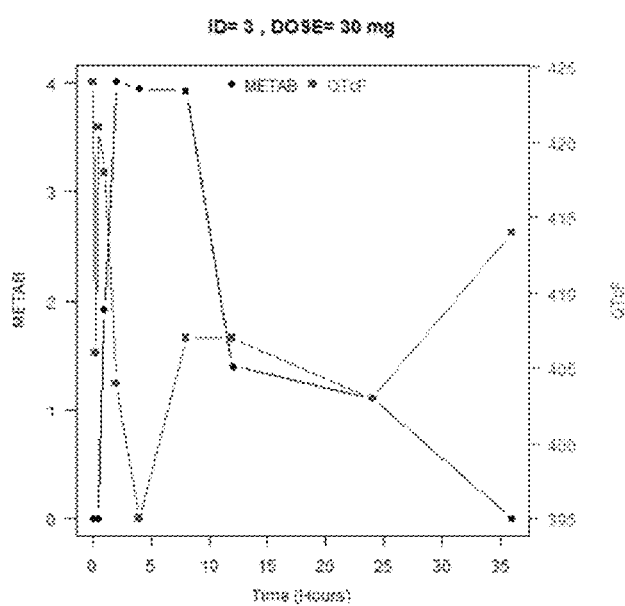

Examination of data indicated no delay in QTc response in relation to the time of peak ANAVEX 2-73 concentration (FIG. 12A), and a similar pattern with the metabolite ANAVEX 19-144 (FIG. 12B).

The final exposure-QTcF model was given by:

$$QTcF_{ij} = 407 + 0.196 \cdot Parent - 0.643 \cdot Metabolite - 0.143 \cdot Time,$$

where is $QTcF_{ij}$ is subject-level QTcF, Parent refers to ANAVEX 2-73, and Metabolite refers to ANAVEX 19-144.

Figure 13A:
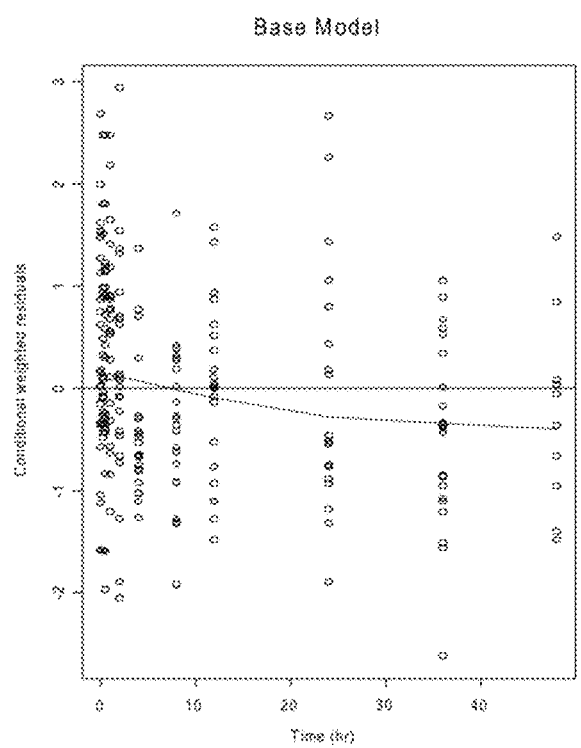
Figure 13B:
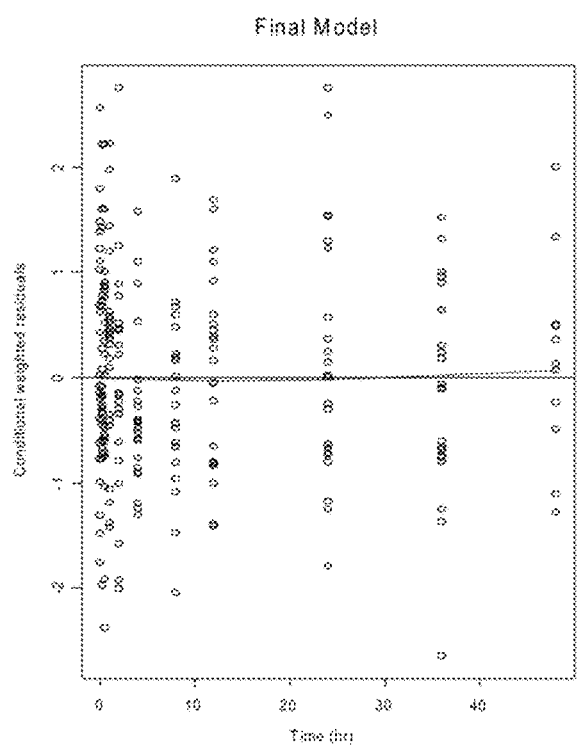
Figure 14A:
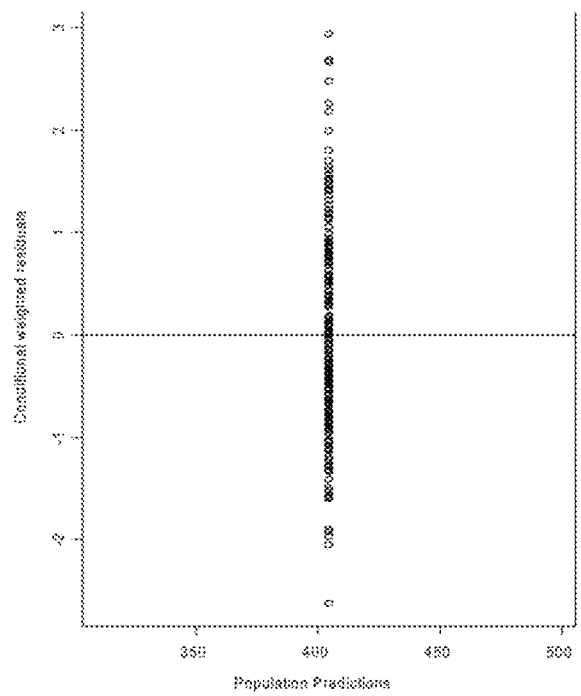
FIG. 14A-B is a Goodness-of-Fit Plot Showing Improved Population Predictions from the Final (FIG. 14B) Model Compared with Base Model (FIG. 14A).
Figure 14B:
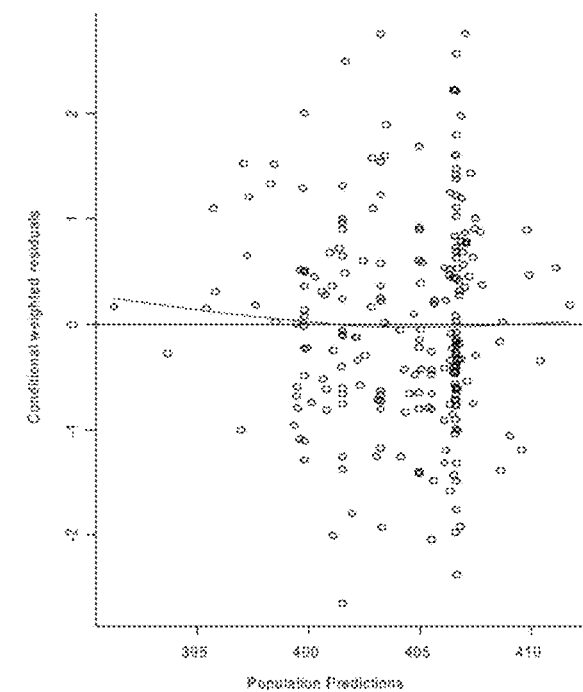
Figure 15A:
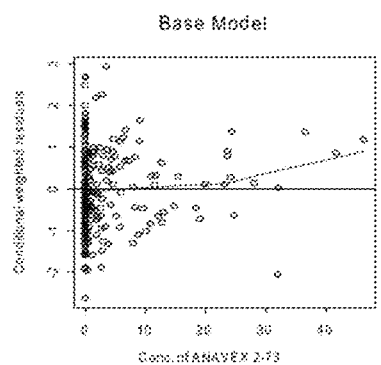
FIG. 15A is a Based Model Plot for A2-73.
Figure 15C:
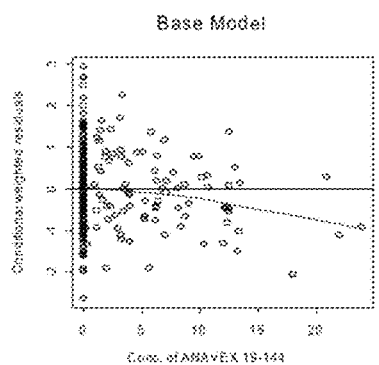
FIG. 15C is a Based Model Plot for A19-144.
Figure 15E:
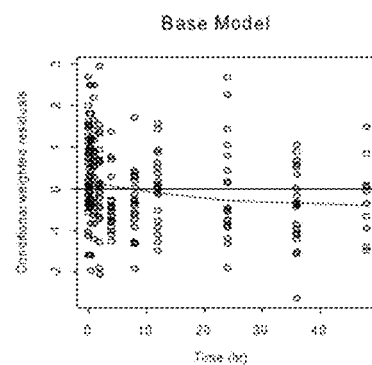
FIG. 15E is a Based Model Plot based on Time.
Figure 15B:
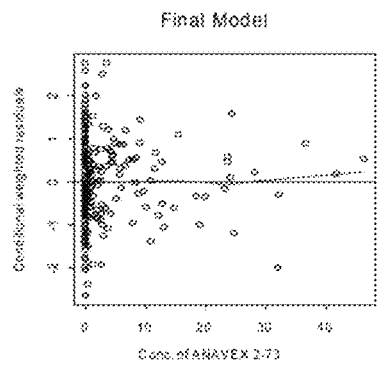
FIG. 15B is a Final Model for A2-73.
Figure 15D:
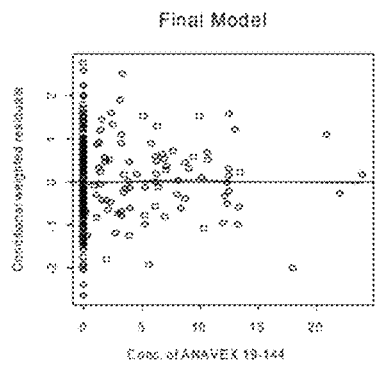
FIG. 15D is a Final Model for A19-144.
Figure 15F:
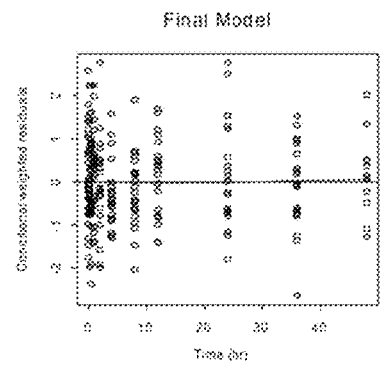
FIG. 15F is a Final Model based on Time.

FIG. 13B is the final model (FIG. 13A Base Model) of a linear exposure-QTcF model with all the variables (parent, metabolite, and time) and is the preferred model for characterizing the QTcF data. The population predictions from the final model (FIG. 14B) show significant improvement from the base model (FIG. 14A) with only the baseline QTcF. The variability in the dataset is explained by inclusion of all the three variables (parent, metabolite, and time) in the model (FIGS. 15 A-F).

Estimates are employed to apply the Exposure-QTcF relationship using observed and unlikely to be observed concentrations of the parent drug and metabolite QTc intervals are predicted, given the parameter estimates obtained with the exposure-QTcF model developed. Assuming the highest C max of 91.36 ng/mL for ANAVEX 2-73 observed in a subject in a phase 2a study for the 50 mg dose (Table 3) and a dose-proportionality factor of 0.085 for C max, the predicted C max for a 200 mg dose is 102.78 ng/mL. Assuming that the corresponding C max of ANAVEX 19-144 is 22.12 ng/mL, a doubling from 11.06 ng/mL was observed for the subject who had a 91.36 ng/mL concentration of ANAVEX 2-73, the predicted QTcF is 412.77 ms at the 200 mg dose. Similarly, assuming that a C max of 131.0 ng/mL is obtained at the 60 mg dose for a subject and the dose is increased 3.3 times to 200 mg, the subject is predicted to have a C max of 145.10 ng/mL. The predicted QTcF for that subject is 410.67 ms, given the corresponding concentration of ANAVEX 19-144 being 38.3 ng/mL (Table 3). Thus, the QT corrected interval upon treatment with ANAVEX 2-73 is predicted to be below 420 ms.

TABLE 3

Predicted QTcF Using Parameter Estimates from the exposure-QTcF model

| Time[d] (hr) | ANAVEX 2-73 Concentration (ng/mL) | ANAVEX 19-144 Concentration (ng/mL) | Baseline QTcF (ms) | Predicted QTcF (ms) |
|---|---|---|---|---|
| 1 | 46.25[a] | 23.96[a] | 407 | 400.52 |
| 1 | 90.68[b] | 23.15[b] | 407 | 409.74 |
| 1 | 106[b] | 31.2[b] | 407 | 407.57 |
| 1.5 | 90.68[b] | 23.15[b] | 407 | 409.67 |
| 1.5 | 91.36[b] | 11.06[b] | 407 | 417.58 |
| 3.5 | 16.05[b] | 35.68[b] | 407 | 386.70 |
| 1.5 | 102.78[c] | 22.12[c] | 407 | 412.77 |
| 1 | 145.1[c] | 36.25[c] | 407 | 410.67 |

[a]Observed Cmax values for ANAVEX 2-73 and ANAVEX 19-144 from the QTc analysis dataset
[b]pairs of the highest observed Cmax values of ANAVEX 2-73 and ANAVEX 19-144 obtained in some patients in the phase 2a studies in Alzheimer's disease patients
[c]predicted concentrations
[d]Time for peak concentration
[e]pairs of extreme values of values of ANAVEX 2-73 and ANAVEX 19-144 not likely to be observed in patients. These values are expected 200 mg as explained in the text above.

Figure 16:
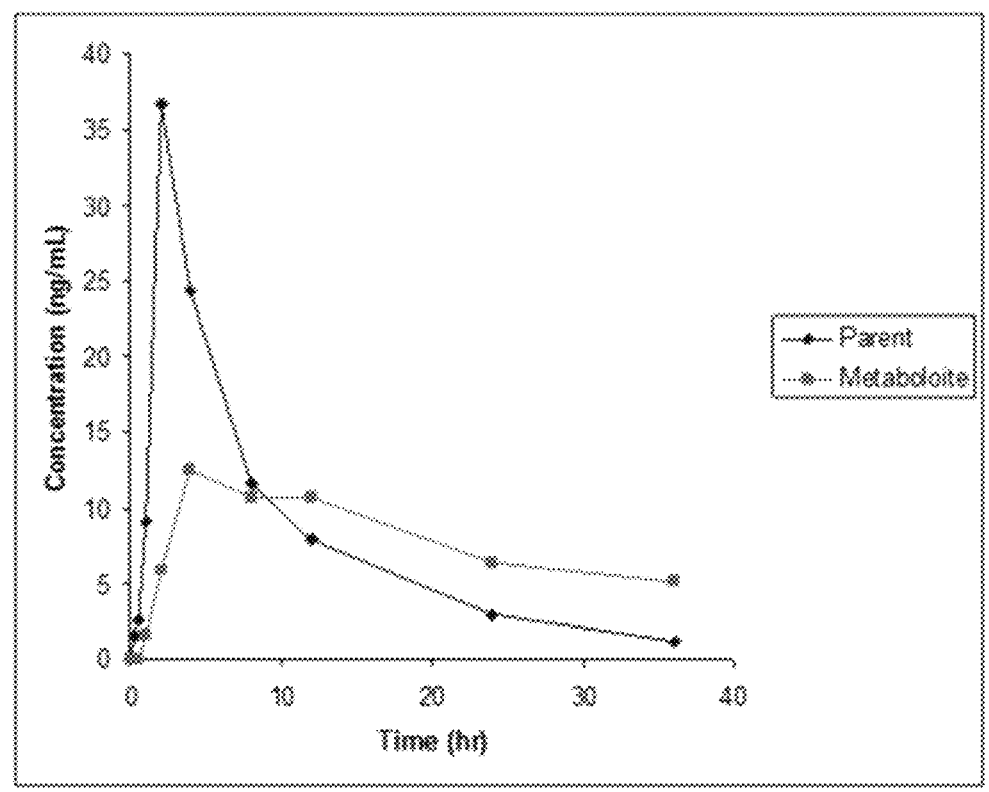
FIG. 16 is a graph of a Typical Concentration-Time for Parent Drug (A2-73) and Metabolite (A19-144) for a Subject Following 60 mg A2-73 Administered Orally.
Figure 17A:
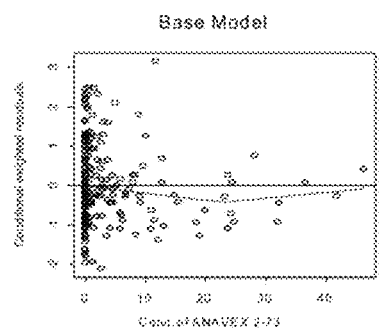
Figure 17C:
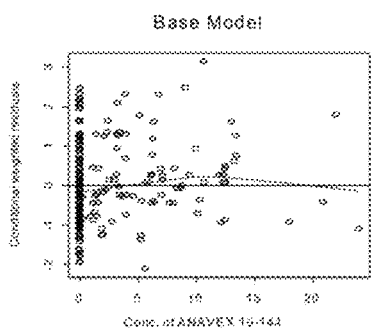
Figure 17E:
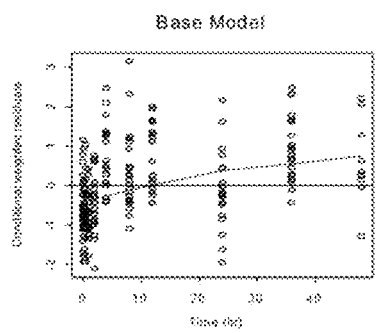
Figure 17B:
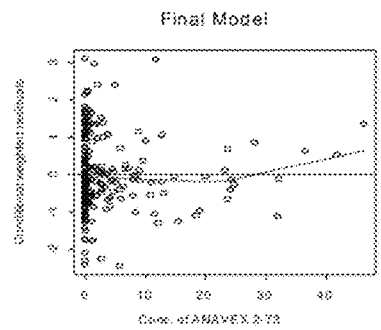
Figure 17D:
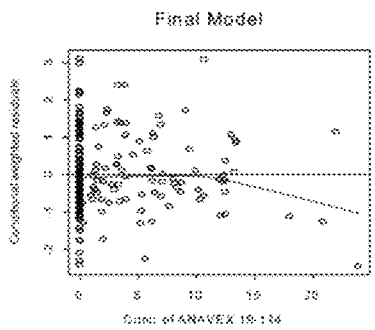
Figure 17F:
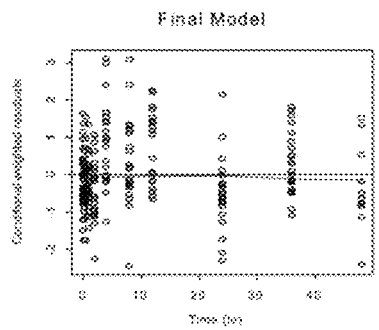

Further modeling characterizes the exposure-heart rate relationship. The dependent variables for the model were ANAVEX 2-73 and ANAVEX 19-144 concentrations, and time. The baseline heart rate was also estimated. The best model developed to explain the exposure-heart rate relationship included all three variables. Again, ANAVEX 2-73 concentration by itself was not initially biologically QT active, but became active as metabolized to A19-144 in the model. The results of the model developed are summarized in Table 4 and FIG. 16. At about 4 to 8 hours post administration A19-144 peaks and surpasses A2-73 at about 8 hours post administration. The results are that ANAVEX 2-73 and ANAVEX 19-144 had opposite initial effects on heart rate. The metabolism of A2-73 to A19-144 modifies this effect. The goodness-of-fit plot in FIG. 17 shows the adequacy of the model in characterizing the exposure-heart rate relationship. It is important to note the upward and negative inflexions in the parent compound and the active metabolite in the final model, respectively, are not indicative of model misspecification but are due to the sensitivity of smoothing loess regression (red line in FIG. 17) to outlying observations in the y-axis. The final model is given below:

$$HR_{ij} = 56.5 - 0.106 \cdot Parent + 0.369 \cdot Metabolite + 0.153 \cdot Time$$

where $HR_{ij}$ is subject specific heart rate, Parent refers to ANAVEX 2-73, and Metabolite is for ANAVEX 19-144.

TABLE 4

A Summary of the Linear Exposure-Heart Rate Model Parameter Estimates

| Parameter | Estimate | SE | % RSE | 95% NONMEM Asymptotic CI | Shrinkage (%) |
|---|---|---|---|---|---|
| Baseline (beats/min) | 56.5 | 1.59 | 2.8 | (53.4, 59.6) | |
| Slope on parent (beats/min/ng/mL) | −0.106 | 0.0375 | 35.4 | (−0.179, −0.033) | |
| Slope on metabolite (beats/min/ng/mL) | 0.369 | 0.0714 | 19.3 | (0.229, 0.509) | |
| Slope on time | 0.153 | 0.0313 | 20.5 | (0.092, 0.214) | |
| $w^2$ (IIV (%) on Baseline) | 35.1 (10.5%) | 16.3 | 46.4 | (3.15, 67.0) | 0.0 |
| $s^2$ (SD) | 26.9 (5.19) | 2.9 | 10.8 | (21.2, 32.6) | 3.6 |

Observed and unlikely to be observed concentrations of the parent drug and metabolite are used to predict heart rate, given the parameter estimates obtained with the exposure-heart rate model developed. Assuming the highest C max of 91.36 ng/mL for ANAVEX 2-73 observed in a subject in a phase 2a study for the 50 mg dose and a dose-proportionality factor of 0.085 for C max, the predicted C max for a 200 mg dose is 102.78 ng/mL. Assuming that the C max of ANAVEX 19-144 is 22.12 ng/mL, a doubling from 11.06 ng/mL observed for the subject who had a 91.36 ng/mL concentration of ANAVEX 2-73 (Table 5), the predicted heart rate is 54.00 beats/min at the 200 mg dose. Similarly, assuming that a C max of 131 ng/mL is obtained at the 60 mg dose for a subject and the dose is increased 3.3 times to 200 mg, that subject is predicted to have a C max of 145.10 ng/m L. The predicted heart rate for that subject is 54.74 beats/min, if the corresponding concentration of ANAVEX 19-144 is 36.5 ng/mL (Table 5). Thus, the heart rate upon treatment with ANAVEX 2-73 is predicted to be below 75 beats/min.

TABLE 5

Predicted Heart Rate Using Parameter Estimates from Table 4

| Time[c] (hr) | ANAVEX 2-73 Concentration (ng/mL) | ANAVEX 19-144 Concentration (ng/mL) | Estimated Baseline Heart Rate (beats/min) | Predicted Heart Rate (beats/min) |
|---|---|---|---|---|
| 1.0 | 46.25[a] | 23.96[a] | 56.5 | 60.59 |
| 1.0 | 90.68[b] | 23.15[b] | 56.5 | 55.58 |
| 1.0 | 106.00 [b] | 31.20[b] | 56.5 | 56.93 |
| 1.0 | 131.25 [b] | 12.49[b] | 56.5 | 47.35 |
| 1.5 | 90.68 [b] | 23.15[b] | 56.5 | 55.66 |
| 1.5 | 91.36 [b] | 11.06[b] | 56.5 | 51.13 |
| 3.5 | 16.05 [b] | 35.68[b] | 56.5 | 68.50 |
| 1 | 145.1 | 36.5 | 56.5 | 54.74 |
| 1.5 | 102.78 | 22.12 | 56.5 | 54.00 |

Source: Calculated from model parameters in Appendix B-8

Figure 18:
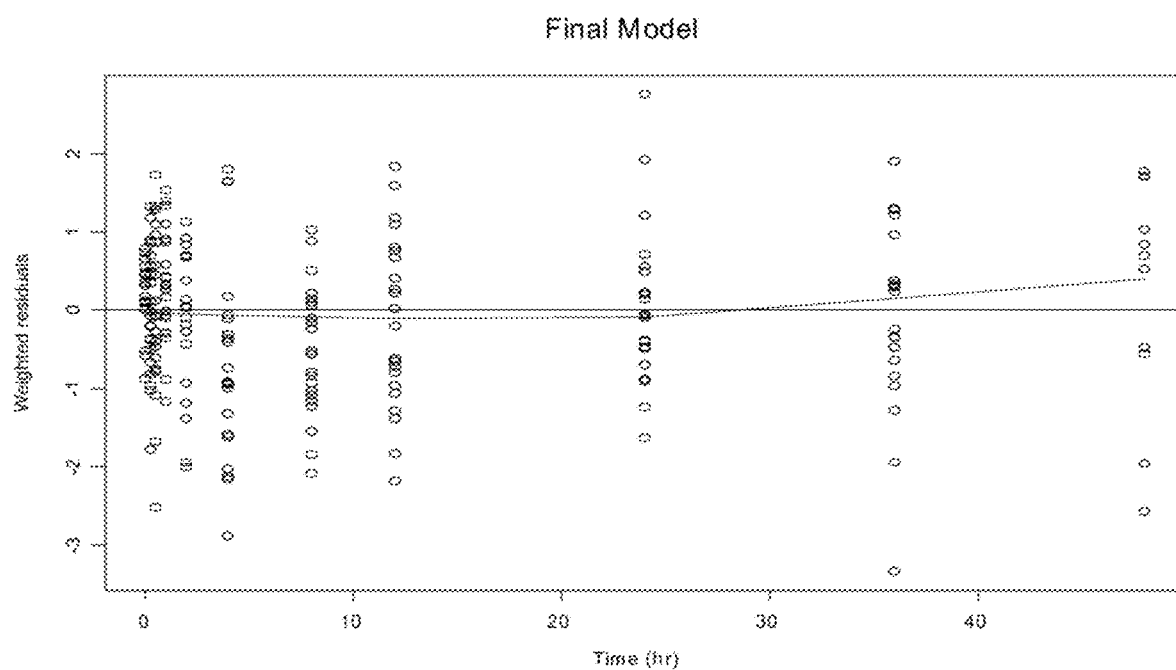
FIG. 18 is a Weighted-Time Plot for the Time-dQTcF Relationship.

The exposure-dQTcF was calculated based on the models described above, concentrations of ANAVEX 2-73 and ANAVEX 19-144, and time were variables tested in the model. The baseline dQTcF is fixed to zero. Only time is retained in the final model. Using goodness-of-fit diagnostics, the linear model of time is employed. Adequacy of the model is demonstrated in FIG. 18. The upward trend of the smoothing loess regression line is driven by the density of points in the positive direction of the y-axis at 48 hr.

Anti-arrhythmic doses of A2-73 from daily to weekly are noted with particular reference to every other day to every third day. Doses from about 10 to about 80 mg are noted with particular reference to about 30 mg, about 40 mg and about 60 mg. When combined with other anti-arrhythmic drugs, lower doses of A2-73 and A19-144 are contemplated. Such reduction may, in particular embodiments, be about one-half to about one-quarter of the above noted dosages.

Example 1

Treatment of Atrial Fibrillation with A2-73

The safety, tolerability, and short term efficacy of ANAVEX 2-73 in human subjects with sustained atrial fibrillation (AF) is demonstrated as follows. A 57 year old male subject with symptomatic AF (72 hr duration) receives 30 mg of A2-73 orally every day. Dosing is initiated in hospital and continues in weekly follow-up visits. Efficacy is assessed as absence of AF recurrence on weekly 12-lead ECG and daily transtelephonic monitoring during the study.

From the start of dosing to the end of the 30 day follow-up period, no serious adverse events occur and AF ceases within 12 hrs and does not recur.

Example 2

Treatment of Atrial Flutter with A2-73

The safety, tolerability, and short term efficacy of ANAVEX 2-73 in human subjects with sustained atrial flutter as follows. A 48 year old female subject with atrial flutter (72 hr duration) receives 60 mg of A2-73 orally daily. Dosing is initiated in hospital and continues in weekly follow-up visits. Efficacy is assessed as absence of atrial flutter recurrence on weekly 12-lead ECG and daily transtelephonic monitoring during the study.

From the start of dosing to the end of the 30 day follow-up period, no serious adverse events occur and AF ceases within 12 hrs and does not recur.

Example 3

Treatment of Ventricular Fibrillation with A19-144

The safety, tolerability, and short term efficacy of ANAVEX 2-73 in human subjects with sustained ventricular fibrillation is demonstrated as follows. A 57 year old male subject with symptomatic ventricular fibrillation (72 hr duration) receives 40 mg of A19-144 orally daily in two 20 mg doses. Dosing is initiated in hospital and continues in weekly follow-up visits. Efficacy is assessed as absence of ventricular fibrillation recurrence on weekly 12-lead ECG and daily transtelephonic monitoring during the study.

From the start of dosing to the end of the 30 day follow-up period, no serious adverse events occur and ventricular fibrillation ceases within 12 hrs and does not recur.

Example 4

Treatment of Atrial Fibrillation with A2-73

The safety, tolerability, and short term efficacy of ANAVEX 2-73 in human subjects with sustained atrial fibrillation (AF) is demonstrated as follows. A 60 year old male subject with symptomatic AF (72 hr duration) is administered intravenously 30 mg of A2-73 every day. Dosing is initiated in hospital and continues in weekly follow-up visits. Efficacy is assessed as absence of AF recurrence on weekly 12-lead ECG and daily transtelephonic monitoring during the study.

From the start of dosing to the end of the 30 day follow-up period, no serious adverse events occur and AF ceases within 12 hrs and does not recur.

Intra venous dosing of A2-73 and A19-144 are therapeutic options of particular note. Specific intravenous (i.v.) doses are arrived at empirically and under the supervision of a medical professional. Doses will vary with specific subjects. Experientially a therapeutically effective i.v. dose is about 30% by weight of an oral dose. Data suggest that a 20 mg oral dose correlates with about a 6 mg i.v. dose and a 60 mg oral dose correlates with about a 17 mg i.v. dose. Notably, therapeutically effective i.v. doses my vary ±40% or more.

The pharmacologically active compositions of this disclosure can be processed in accordance with conventional methods of Galenic pharmacy to produce medicinal agents for administration to patients, e.g., mammals including humans.

The compositions of this disclosure can be employed in admixture with conventional excipients, i.e., pharmaceutically acceptable organic or inorganic carrier substances suitable for parenteral, or enteral (e.g., oral or inhalation) use which do not deleteriously react with the active compositions. Suitable pharmaceutically acceptable carriers include but are not limited to water, salt solutions, e.g., saline. The pharmaceutical preparations can be sterilized and if desired mixed with auxiliary agents, e.g., salts for influencing osmotic pressure, buffers and the like which do not deleteriously react with the active compositions. They can also be combined where desired with other active agents, e.g., cardiac agents to reduce or control long QT syndrome. Beta-blockers are noted class of drugs for such therapy e.g., nadolol (Corgard) and propranolol (Inderal LA, InnoPran XL). Note is also made of mexiletine, rufinamide and spironolactone. It is further contemplated that additional pharmaceuticals to reduce or control long QT syndrome will be developed that are similarly applicable.

In some embodiments, dosage forms include instructions for the use of such compositions.

For parenteral application, particularly suitable are injectable (including intravenous), sterile solutions, preferably oily or aqueous solutions, as well as suspensions, emulsions, or implants, including suppositories. Ampules are convenient unit dosages.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions are dispensed in unit dosage form comprising about 1 to about 100 mg in a pharmaceutically acceptable carrier per unit dosage.

The dosage of the compositions according to this disclosure generally are 0.4 to 1 mg/kg/day, preferably 0.4 to 0.8 mg/kg/daily. Particular reference is made to doses of about 20 mg to about 60 mg per day. Unit dosage forms of from about 25 mg to about 1 gram are noted with particular reference to dosage forms of from about 20 mg to about 60 mg.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

The terms "effective amount" or "therapeutically effective amount" as used herein, is to be broadly understood to encompass both a sufficient amount of at least one agent being administered which achieve a desired result, e.g., to relieve to some extent one or more symptoms of a disease or condition being treated as well as a to prevent the occurrence of one or more symptoms of a disease or condition being treated (a prophylactically effective amount). In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study. The term "prophylactic" or "prophylaxis" shall mean preventing or reducing the likelihood that a disease, condition or event will occur. A treatment will be considered therapeutically prophylactic if a subject is asymptomatic for at least about 30 days or if there is a reduction in episodes of at least about 50% over a 30 day period as compared with pre-treatment rate of occurrence.

The invention claimed is:

1. A method for treating a cardiac dysfunction, comprising administering to a subject in need thereof a therapeutically effective amount of ANAVEX 19-144, a pharmaceutically acceptable salt thereof, or a combination of ANAVEX 19-144 or a pharmaceutically acceptable salt thereof with ANAVEX 2-73;
   wherein the subject's QT interval is shortened by the shorter of about 10 ms (milliseconds) and by about 2% to about 3%, relative to the subject's QT interval before the administration; and
   wherein the QT interval is a measure of time between the start of the Q wave and the end of the T wave in the heart's electrical cycle.

2. The method of claim 1, wherein said cardiac dysfunction is selected from the group consisting of cardiac arrest-related dysfunction including cardiac arrhythmia, premature ventricular contraction (PVC) induced left ventricular dysfunction, atrial fibrillation, atrial flutter, induced left ventricular dysfunction, ventricular arrhythmia including ventricular tachycardia and fibrillation, and a combination thereof.

3. The method of claim 1, wherein said cardiac dysfunction is ventricular arrhythmia.

4. The method of claim 1, wherein said cardiac dysfunction is atrial arrhythmia.

5. The method of claim 1, wherein said administering to a subject is a therapeutically effective amount of ANAVEX 19-144 daily.

6. The method of claim 5, wherein said therapeutically effective amount is from about 20 mg to about 60 mg when administered orally.

7. The method of claim 6, wherein said therapeutically effective amount is two daily doses of about 20 mg to about 30 mg each.

8. The method of claim 6, wherein said therapeutically effective amount is two daily doses of about 20 mg each.

9. The method of claim 6, wherein said therapeutically effective amount is administered in a single daily dosage of about 40 mg to about 60 mg.

10. The method of claim 5, wherein said therapeutically effective amount is from about 6 mg to about 17 mg when administered intravenously.

11. The method of claim 10, wherein said therapeutically effective amount is about 8 mg when administered intravenously.

12. The method of claim 10, wherein said therapeutically effective amount is about 10 mg when administered intravenously.

13. The method of claim 10, wherein said therapeutically effective amount is about 15 mg when administered intravenously.

14. A method of treating ventricular fibrillation in a subject in need thereof, comprising administering to the subject an effective amount of ANAVEX 19-144.

15. The method of claim 14, wherein the effective amount of ANAVEX 19-144 is about 40 mg to about 60 mg when administered orally.

16. The method of claim 14, wherein the effective amount of ANAVEX 19-144 is about 20 mg twice daily when administered orally.

* * * * *